Figures 3, 4:
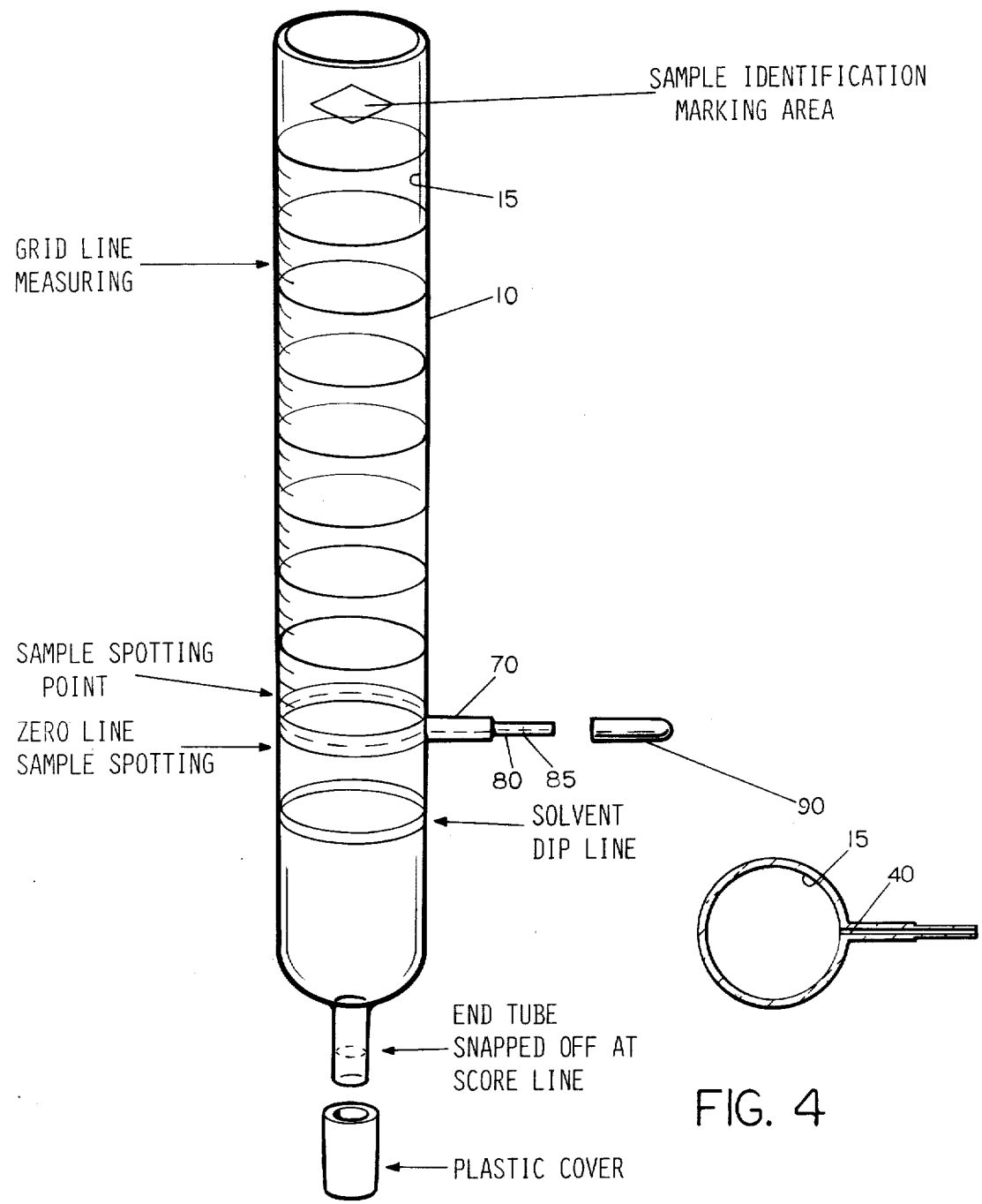

United States Patent [19]

Wisebaker et al.

[11] 4,384,958
[45] May 24, 1983

[54] THIN LAYER CHROMATOGRAPHY DEVICE AND METHOD OF MAKING CHROMATOGRAPHY TEST

[75] Inventors: Sandra M. Wisebaker, Toledo, Ohio; Paul L. White, Ida, Mich.

[73] Assignee: Owens-Illinois, Inc., Toledo, Ohio

[21] Appl. No.: 352,618

[22] Filed: Feb. 26, 1982

[51] Int. Cl.³ ............................................. B01N 15/08
[52] U.S. Cl. ................................ 210/658; 210/198.3; 422/70
[58] Field of Search ................ 210/658, 198.3; 422/70

[56] References Cited

U.S. PATENT DOCUMENTS

| | | | |
|---|---|---|---|
| 3,387,710 | 6/1968 | Pogacar | 210/198.3 |
| 3,513,092 | 5/1970 | Matherne, Jr. | 210/198.3 |
| 3,623,602 | 11/1971 | Valente | 210/198.3 |
| 4,205,058 | 5/1980 | Wagner et al. | 210/658 |
| 4,273,653 | 6/1981 | Uihlein | 210/658 |

Primary Examiner—John Adee
Attorney, Agent, or Firm—Richard D. Heberling; Myron E. Click; David H. Wilson

[57] ABSTRACT

There is disclosed a thin layer chromatography device comprising a transparent tube, a coating of adsorbent on the inside of the tube to provide a thin chromatography layer, one end of the tube narrowed down to form a neck with a score line thereon for breaking the neck, the other end of the tube being sealed to provide a hermetically sealed chromatography device, there being at least one small opening in the tube near the neck end of the tube for providing means to insert a sample into the tube on the thin chromatography layer and for providing means to form an air vent to the inside of the tube when the neck end is broken and placed in a solvent.

11 Claims, 4 Drawing Figures

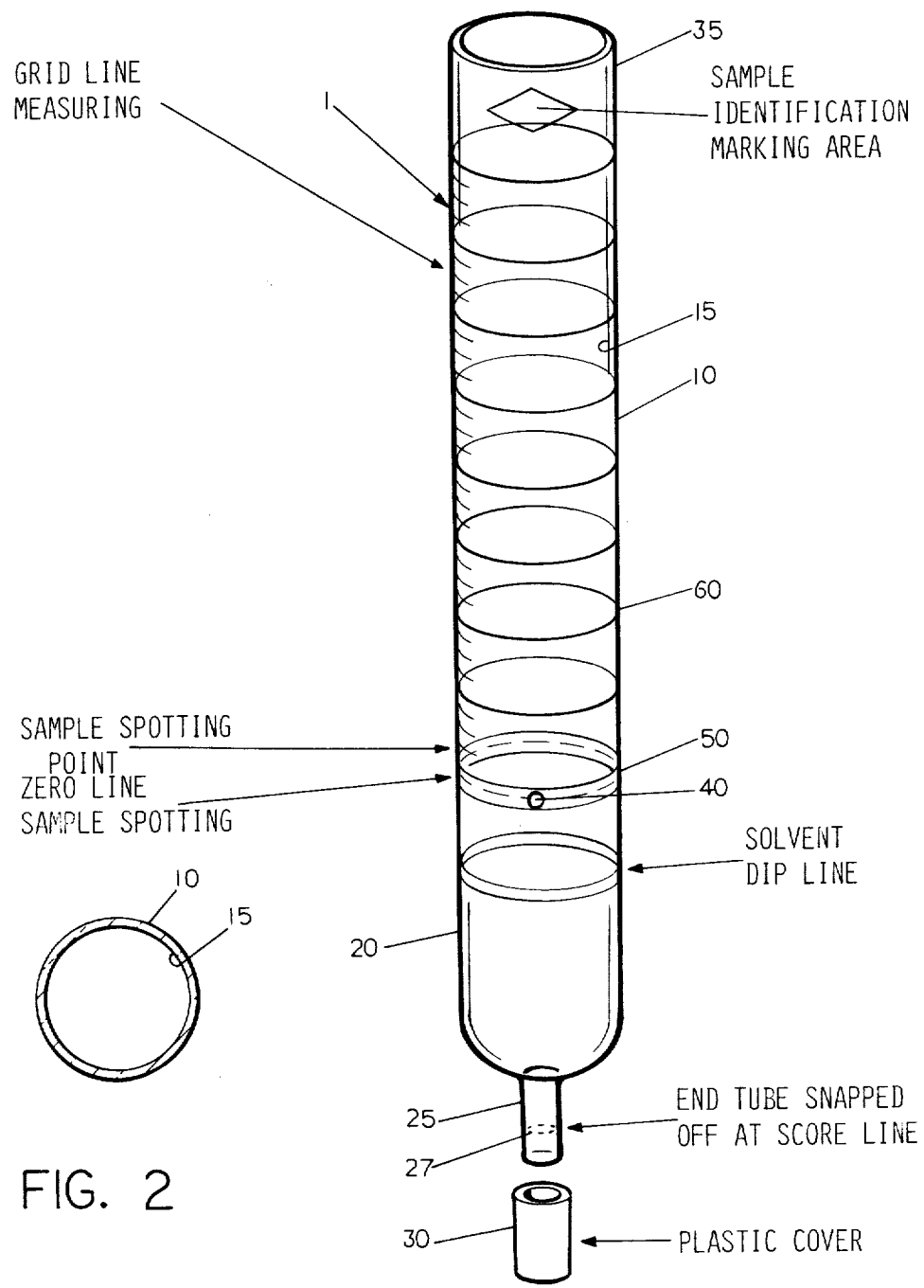

THIN LAYER CHROMATOGRAPHY DEVICE AND METHOD OF MAKING CHROMATOGRAPHY TEST

The present invention is directed to a thin layer chromatography device and method of making a chromatography test using the device which is in a transparent tubular form which includes a thin adsorbent layer coated on the inside of the tube.

Thin layer chromatography is a technique for separating chemical compounds by means of a thin layer of adsorbent material. In the past a thin layer of adsorbent material was coated onto a supporting flat plate and the tests conducted thereon. Thin layer chromatography is based on the principles of adsorption, partition, and ion exchange chromatography. A combination of several mechanisms is usually involved, although adsorption is the most common.

When the above described coated plate is immersed in a small quantity of solvent in the bottom of a tank, capillary action causes the solvent to move up the plate through the adsorbent. Continuous competition for active adsorbent sites by the sample and solvent produces fractionization of the sample. Hence components of the sample move different distances along the plate depending upon the affinity for the adsorbent in the solvent. The migration of a component is measured by the $R_f$ value. It is computed by dividing the distance the component travels by the distance the solvent travels.

U.S. Pat. No. 3,387,710 to Pogacar shows a tube of a transparent material such as glass, the tube having an activated adsorbent coating on its inner surface. The tube has air tight seals at the ends. There are disadvantages and difficulties encountered with the use of such a tubular carrier including the lack of speed, lack of convenience, and inefficiency of chromatography test.

Hence it is desirable to provide a thin layer chromatography device that can serve as an efficient and easily used preliminary screening tool, the screening tool being very useful in the ultimate choice of a more sensitive analytical method.

It is an object of the present invention to provide a thin layer chromatography device comprising a transparent tube, a coating of adsorbent on the inside of the tube to provide a thin chromatography layer, one end of the tube narrowed down to form a neck with a score line thereon for breaking the neck, the other end of the tube being sealed to provide a hermetically sealed chromatography device, there being at least one small opening in the tube near the neck end of the tube for providing means to insert a sample into the tube on the thin chromatography layer and for providing means to form an air vent to the inside of the tube when the neck end is broken and placed in a solvent.

It is an object of the present invention to provide a thin layer chromatography device comprising a glass tube, a coating of adsorbent and/or binder on the inside of the tube to provide a thin chromatography layer, at least one end of the tube narrowed down to form a neck with a score line thereon for breaking the neck, both ends of the tube being sealed to provide a hermetically sealed tube, a small sealed opening near the neck end of the tube that can be unsealed to form an air vent to the inside of the tube, the opening being located nearer the narrowed end of the glass tube than the other end, the small opening adapted for inserting a sample inside the tube to thereby contact the coating on the inside thereof.

It is an object of the present invention to provide a method of making a chromatography test using a thin layer chromatography device comprising a glass tube with a chromatography coating of adsorbent and/or binder on the inside thereof, the glass having a narrowed neck end adapted for breaking to let solvent in, there being a small opening on the tube near the neck end for providing a sample and air to the interior of the tube, the method comprising the steps of:

A. inserting a sample through the small opening to the thin chromatography layer in the tube,
B. breaking the narrow end of the tube, and
C. placing the neck end of the tube in solvent for development of the sample on the thin layer.

It is an object of the present invention to provide a method of making a chromatography test including the steps of:

A. inserting a sample into the interior of a glass tube having an adsorbent coating on the inside thereof through a small opening in the tube to contact the thin chromatography layer,
B. breaking a narrow neck end of the tube with a score line provided thereon,
C. placing the neck end of the tube in solvent for development of the sample on the thin layer,
D. measuring the distance the solvent travels, and
E. measuring the distance the sample travels on the thin layer.

These and other objects will be apparent from the specification that follows, the appended claims and the drawings in which:

FIG. 1 is a perspective view of a thin layer chromatography device of the present invention,
FIG. 2 is a sectional view of the device of FIG. 1,
FIG. 3 is a perspective view of a different embodiment of the chromatography device of the present invention, and
FIG. 4 is a cross-sectional view of the device of FIG. 3.

The present invention provides an outstanding, easy-to-use thin layer chromatography device comprising a transparent tube, a coating of adsorbent on the inside of the tube to provide a thin chromatography layer, one end of the tube narrowed down to form a neck with a score line thereon for breaking the neck, the other end of the tube being sealed, at least one small opening in the tube near the neck end for providing means to insert a sample into the tube on the thin layer and for providing means to form an air vent to the inside of the tube when the neck is broken and placed in the solvent.

The present invention also provides an outstanding efficient method of making a chromatography test using a thin layer chromatography device comprising a transparent tube with a chromatography coating of adsorbent and/or binder on the inside thereof, the tube preferably being made of glass and having a narrowed neck end adapted for breaking to let solvent in, there being a small opening on the tube near the neck end for providing a sample and air to the interior of the tube, the method comprising the steps of:

A. inserting a sample through the small opening to the thin chromatography layer,
B. breaking the narrow end of the tube, and
C. placing the neck end of the tube in solvent for development of the sample on the thin layer.

The method of the present invention also includes the further step of measuring the distances of the solvent and sample travel on the thin layer.

As seen in FIG. 1 there is provided a thin layer chromatography device 1 comprising a transparent tube 10 preferably made of glass although it can be made of a transparent plastic material such as polymethyl methacrylate, polyester, nylon, polycarbonate, or other clear plastic material. An adsorbent and/or binder coating 15 is provided for the chromatography test in which the distance traveled by a solvent and the distance traveled by a sample is easily measured with the outstanding device 1 of the present invention. One end of the tube 20 is provided with a narrowed end 25 with a score line 27 for easy breaking. There is provided a plastic cover 30 to cover the end of the tube to keep the end of the tube clean before use and, afterward, to keep the sample clean, it normally being hermetically sealed before use. The other end of the tube 35 is also provided with sealing means that is preferably a closed rounded end of the tube to keep the sample hermetically sealed.

In accordance with the present invention there is at least one small opening 40 in the tube for spotting the sample and getting the sample on to the thin layer coating on the inside of the tube. The opening 40 is important because it also provides means to form an air vent on the inside of the tube when the neck end is broken and placed in a solvent to begin the test. The end of the tube 35 remains sealed during use.

As seen in FIG. 1, there is a zero line for sample spotting, the line being located at 50. There are also indicia 60 on the sides of the tubes so that the distance the sample travels and the distance the solvent travels is easily measured once the end 25 is broken and placed in solvent. As seen in FIG. 3, which is a different embodiment of the device, the device shown in FIG. 3 differs from that of FIG. 1 mainly by the arrangement and location of the small sample opening. In FIG. 3 there is provided a small side tube 70 with a narrowed end 80 having a score line 85, the small side tube being easily broken to provide access for a sample to the inside of the tube and also to provide means for a vent to the inside of the tube when the end of the tube is broken and placed in solvent and to keep the sample clean after testing. A plastic cover 90 is provided to cover the side tube 70 and provide the hermetic seal after the device is used for testing.

As seen in FIGS. 1 and 3, the present invention provides an adsorbent that is encapsulated preferably in a glass tube with highly advantageous grid markings for easy measurement of the distances that the sample and solvent travel on the adsorbent layer. These distances are easily measured by visual inspection and the sample is easily placed on the zero starting line. Hence, the samples are accurately placed inside the tube to provide an easy, convenient and accurate preliminary screening test.

As is well known in the art, suitable adsorbents include silica gel based adsorbents, aluminum oxide, microcrystalline cellulose and silica gel containing phosphor. The adsorbent coating with or without a binder is generally about 0.2 to 0.5 mm in thickness, the preferred thickness being generally about 0.25 to 0.3 mm.

As is known in the art, the adsorbent coating such as one made of silica gel can be activated by heating, say for one hour at 100° C. or more. Thus the tube is dried to activate the adsorbent and the tube can be used without further treatment because it is hermetically sealed.

As is known in the art, solvents used in chromatography tests include heptane, cyclohexane, carbon tetrachloride, benzene, chloroform, diethyl ether, ethyl acetate, acetone, methanol and water.

What is claimed is:

1. A thin layer chromatography device comprising a transparent tube, a coating of adsorbent on the inside of the tube to provide a thin chromatography layer, one end of the tube narrowed down to form a neck with a score line thereon for breaking the neck, the other end of the tube being sealed, at least one small opening in the tube near the neck end of the tube for providing means to insert a sample into the tube on the thin chromatography layer and for providing means to form an air vent to the inside of the tube when the neck end is broken and placed in a solvent.

2. A device as defined in claim 1 in which there are indicia on the outside of the tube including a zero line with the small opening on it for spotting the sample.

3. A device as defined in claim 1 in which there is a solvent dip line as indicia on the tube located between the small opening and the neck end.

4. A thin layer chromatography device comprising a glass tube, a coating of adsorbent on the inside of the tube to provide a thin chromatography layer, one end of the tube narrowed down to form a neck with a score line thereon for breaking the neck, the other end being sealed, a small sealed opening that can be unsealed to form an air vent to the inside of the tube, the opening being located nearer the narrowed end of the glass tube than the other end, the small opening adapted for inserting a sample inside the tube to contact the coating on the inside.

5. A thin layer chromatography device comprising a glass tube, a thin chromatography coating of adsorbent and binder on the inside of the tube, one end of the tube narrowed down to form a neck with a score line thereon for breaking the neck and allowing solvent to enter the tube, the other end being sealed, a smaller area which can be broken on the side of the tube, this area is located nearer the narrowed end of the glass tube than the other end, there being means for breaking the same and inserting a sample inside the small opening to contact the coating on the inside of the large glass tube; and indicia on the tube to indicate the extent the solvent and the sample travel up the glass when the narrow neck end of the glass tube is broken and solvent enters the large glass tube.

6. A thin layer chromatography device comprising a glass tube, a coating of adsorbent and binder on the inside of the tube to provide a thin chromatography layer, one end of the tube narrowed down to form a neck with a score line thereon for breaking the neck, the other end of the tube adapted for sealing with a cap, a smaller side glass tube projecting from the side of the tube, the side tube located nearer the narrowed end of the glass tube than the other end, and there being means on the side tube for breaking the same and inserting a sample inside the side tube and to contact the coating on the inside of the large glass tube.

7. A method of making a chromatography test using a thin layer chromatography device comprising a glass tube with a chromatography coating of adsorbent on the inside thereof, the glass tube having a narrowed neck end adapted for breaking to let solvent in, there being a small opening on the tube near the neck end for providing a sample and air to the interior of the tube, the method comprising the steps of:

A. inserting a sample thru the small opening to the thin chromatography layer,

B. breaking the narrow neck end of the tube, and

C. placing the neck end of the tube in solvent for development of the sample on the thin layer.

8. A method as defined in claim 7 in which there is the further step of measuring the distances of the solvent and sample travel on the thin layer.

9. A method of making a chromatography test using a thin layer chromatography device, the device comprising a glass tube with a chromatography coating of adsorbent and binder on the inside thereof, the tube having a narrowed end for breaking and a small area which can be broken on the side of the tube, to provide a small opening; the method comprising the steps of:

A. breaking the seal over the small opening,

B. inserting a sample through the small opening onto the coating inside the first tube, C. breaking the narrowed end of the tube, and D. placing the broken end of the tube in solvent for reaction with the sample on the coating.

10. A method of making a chromatography test using a thin layer chromatography device, the method comprising the steps of:

A. providing a first glass tube having a thin chromatography coating of adsorbent on its inside to provide a thin chromatography layer, the glass tube having a narrowed end for breaking, there being a second small side glass tube located near the narrowed end of the first tube, B. inserting a sample into the first tube to contact the coating through a small opening, C. breaking the narrowed end of the first tube, and D. inserting the broken end of the first tube in a solvent for development of the sample on the coating.

11. A method as defined in claims 9 or 10 including the step of measuring the distance traveled by the sample and the distance traveled by the solvent on thin layer coating after the solvent contacts the sample.

* * * * *